US010251998B2

(12) United States Patent
Burkhart et al.

(10) Patent No.: US 10,251,998 B2
(45) Date of Patent: Apr. 9, 2019

(54) STEM CELL DELIVERY SYSTEM

(71) Applicant: Mayo Foundation for Medical Education and Research, Rochester, MN (US)

(72) Inventors: Harold M. Burkhart, Oklahoma City, OK (US); Timothy J. Nelson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 54 days.

(21) Appl. No.: 15/120,268

(22) PCT Filed: Feb. 23, 2015

(86) PCT No.: PCT/US2015/017029
§ 371 (c)(1),
(2) Date: Aug. 19, 2016

(87) PCT Pub. No.: WO2015/127339
PCT Pub. Date: Aug. 27, 2015

(65) Prior Publication Data
US 2017/0056583 A1    Mar. 2, 2017

Related U.S. Application Data

(60) Provisional application No. 61/943,813, filed on Feb. 24, 2014.

(51) Int. Cl.
*A61M 31/00* (2006.01)
*A61M 5/158* (2006.01)
(Continued)

(52) U.S. Cl.
CPC ......... *A61M 5/158* (2013.01); *A61B 17/3478* (2013.01); *A61K 9/0019* (2013.01);
(Continued)

(58) Field of Classification Search
CPC .... A61M 5/3295; A61M 5/3297; A61M 5/46; A61M 5/34; A61M 5/344; A61M 5/345; A61M 5/158; A61M 2005/341; A61M 5/3298; A61M 2005/1581; A61M 5/145; A61M 5/162; A61M 5/1452; A61B 1734/18; A61B 17/205; A61B 2017/00247; A61B 17/3478; A61K 35/12; A61K 9/0019
(Continued)

(56) References Cited

U.S. PATENT DOCUMENTS 2,853,070 A    9/1958  Maurice
5,190,521 A *  3/1993  Hubbard ............... A61M 5/422
                                                  604/117
(Continued)

OTHER PUBLICATIONS

International Search Report and Written Opinion for PCT/US2015/017029, dated May 15, 2015, 14 pages.

*Primary Examiner* — Jason Flick
(74) *Attorney, Agent, or Firm* — Fish & Richardson P.C.

(57) ABSTRACT

This document provides systems and methods that can be used for the practice of regenerative medicine. For example, this document provides devices and methods for injecting stem cell material into tissue, such as heart tissue.

9 Claims, 4 Drawing Sheets

(51) Int. Cl.
  *A61B 17/34* (2006.01)
  *A61K 9/00* (2006.01)
  *A61K 35/12* (2015.01)
  *A61M 5/145* (2006.01)
  *A61M 5/162* (2006.01)
  *A61M 5/32* (2006.01)
  *A61M 5/34* (2006.01)
  *A61B 17/20* (2006.01)
  *A61B 17/00* (2006.01)

(52) U.S. Cl.
  CPC ............ *A61K 35/12* (2013.01); *A61M 5/1452* (2013.01); *A61M 5/162* (2013.01); *A61B 17/205* (2013.01); *A61B 2017/00247* (2013.01); *A61M 5/3298* (2013.01); *A61M 2005/1581* (2013.01); *A61M 2005/341* (2013.01)

(58) Field of Classification Search
  USPC .......................................................... 604/506
  See application file for complete search history.

(56) References Cited

U.S. PATENT DOCUMENTS

| | | |
|---|---|---|
| 5,405,330 A | 4/1995 | Zunitch |
| 5,891,106 A | 4/1999 | Butuzov |
| 6,217,554 B1 | 4/2001 | Green |
| 2008/0294096 A1* | 11/2008 | Uber, III ............... A61M 5/142 604/66 |
| 2013/0131589 A1* | 5/2013 | Mudd .................... A61M 5/19 604/82 |
| 2014/0018835 A1 | 1/2014 | Scherkowski |
| 2015/0157809 A1* | 6/2015 | Park ...................... A61M 5/204 604/131 |

* cited by examiner

STEM CELL DELIVERY SYSTEM

CROSS-REFERENCE TO RELATED APPLICATIONS

This application is a National Stage application under 35 U.S.C. § 371 of International Application No. PCT/US2015/017029, having an International Filing Date of Feb. 23, 2015, which claims the benefit of U.S. Provisional Application Ser. No. 61/943,813, filed Feb. 24, 2014. This disclosure of the prior application is considered part of (and is incorporated by reference in) the disclosure of this application.

BACKGROUND

1. Technical Field

This document relates to systems and methods that can be used for the practice of regenerative medicine. For example, this document relates to devices and methods for injecting stem cell material into tissue, such as heart tissue.

2. Background Information

A primary goal of regenerative medicine is the restoring, maintaining, or enhancing of tissue and organ function. Regenerative medicine, also known as stem cell therapy, is emerging as a potential treatment for cardiovascular diseases, diabetes, degenerative joint conditions, brain and nervous system (neurological) conditions, such as Parkinson's disease, and many other conditions. For example, researchers are studying the possibility of using stem cell therapy to repair or regenerate injured heart tissue to treat many types of cardiovascular diseases, from adult acquired disorders to congenital diseases.

Today, the standard treatment for people with hypoplastic left heart syndrome (HLHS) includes a three-stage surgery that enables the right ventricle to pump blood to the entire body. Though effective, these surgeries are palliative and do not eliminate the person's risk of needing a heart transplant later. Because the right ventricle is not normally called on to support the entire body, the strain imposed on the right ventricle can lead to declines in pumping ability over time. Regenerative medicine strategies for HLHS have the potential to provide an alternative to heart transplantation. Using stem cells of different types and from various sources—including cells from the patient's own body—regenerative therapies for HLHS could replace, rejuvenate or regenerate defective tissues, leaving new, healthy tissues in their place. Such approaches could restore the pumping ability of the right ventricle once it begins to decline or perhaps prevent the decline altogether, postponing or eliminating the need for a future heart transplant.

SUMMARY

This document provides systems and methods that can be used for the practice of regenerative medicine. For example, this document provides devices and methods for injecting stem cell material into tissue, such as heart tissue.

In a first general aspect, this document features a device for injecting stem cell material into a tissue. The device comprises a proximal end coupling portion that is configured to releasably couple with a syringe containing the stem cell material; a barrel that is rigidly coupled to the coupling portion, the barrel including a lumen with a tube therein, the tube being configured to receive and convey the stem cell material when the syringe is activated to dispense the stem cell material therefrom; and a distal end portion that is pivotably coupled to the barrel. The distal end portion includes multiple needles extending distally from a body of the distal end portion. The multiple needles are configured for insertion into the tissue, and the tube is fluidically connected to each individual needle of the multiple needles such that a substantially equal amount of stem cell material will be dispensed from each individual needle when the syringe is activated to dispense the stem cell material therefrom.

In various implementations of the device, the barrel may be pivotable in relation to the distal end portion through an arc of about 180 degrees. Optionally, the multiple needles may include four or more individual needles. In particular embodiments, the multiple needles may include seven or more individual needles.

In a second general aspect, this document features a system for injecting stem cell material into a tissue. The system comprises a syringe that is configured to contain and dispense the stem cell material therefrom and an injection device. The injection device comprises a proximal end coupling portion that is configured to releasably couple with the syringe; a barrel that is rigidly coupled to the coupling portion, the barrel including a lumen with a tube therein, the tube being configured to receive and convey the stem cell material when the syringe is activated to dispense the stem cell material therefrom; and a distal end portion that is pivotably coupled to the barrel, the distal end portion including multiple needles extending distally from a body of the distal end portion. The multiple needles are configured for insertion into the tissue, and the tube is fluidically connected to each individual needle of the multiple needles such that a substantially equal amount of stem cell material will be dispensed from each individual needle when the syringe is activated to dispense the stem cell material therefrom.

In various implementations of the system, the system may further comprise a spacer, the spacer being coupleable to the distal end portion, the spacer being configured to establish a maximum injection depth of the stem cell material into the tissue. In particular embodiments, the barrel may be pivotable in relation to the distal end portion through an arc of about 180 degrees. Optionally, the multiple needles may include four or more individual needles. In particular embodiments, the multiple needles may include seven or more individual needles.

In a third general aspect, this document features a method for injecting stem cell material into a tissue. The method comprises coupling a source of stem cell material to a multi-needle injection device, inserting the multiple needles of the multi-needle injection device into the tissue, and injecting the stem cell material into the tissue. The multi-needle injection device comprises a proximal end coupling portion that is configured to releasably couple with a syringe containing the stem cell material; a barrel that is rigidly coupled to the coupling portion, the barrel including a lumen with a tube therein, the tube being configured to receive and convey the stem cell material when the syringe is activated to dispense the stem cell material therefrom; and a distal end portion that is pivotably coupled to the barrel, the distal end portion including multiple needles extending distally from a body of the distal end portion. The multiple needles are configured for insertion into the tissue, and the tube is fluidically connected to each individual needle of the multiple needles such that a substantially equal amount of stem cell material will be dispensed from each individual needle when the syringe is activated to dispense the stem cell material therefrom.

In various implementations of the method, the method may further comprise adjusting the multi-needle injection device to inject the stem cell material into the tissue at a particular depth. Optionally, the adjusting step may comprise coupling a spacer device to the distal end portion of the multi-needle injection device. In some embodiments of the method, the method further comprises pivoting the barrel in relation to the distal end portion. In particular embodiments, the method may also comprise: removing the multi-needle injection device from the tissue; repositioning the multi-needle injection device to a second tissue area; and injecting the stem cell material into the second tissue area.

Particular embodiments of the subject matter described in this document can be implemented to realize one or more of the following advantages. In some embodiments, the stem cell injection systems and methods provided herein facilitate an even distribution of stem cell injectate. For example, the injection devices are configured to concurrently dispense a substantially equal amount of injectate through each needle of a group of multiple needles. In particular embodiments, the group of multiple needles are evenly spaced from each other to further facilitate an even distribution of injectate. The ability to deliver stem cell material with an even distribution may beneficially lead to a uniform regeneration of tissue. In some embodiments, the stem cell injection systems provided herein include an attachment for establishing and controlling the injection depth as desired for a particular injection site or situation. In some embodiments, the stem cell injection systems provided herein are configured to have only a small amount of residual injectate material remaining in the system after the system has been used. In result, stem cell material is used efficiently when administered using the stem cell injection systems provided herein. For at least the forging reasons, the stem cell injection systems provided herein may facilitate an overall enhanced stem cell injection treatment technique, leading to better patient outcomes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides systems and methods that can be used for the practice of regenerative medicine. For example, this document provides systems and methods for injecting stem cell material into tissue, such as heart tissue. In one example implementation, the systems and methods provided herein can be used as part of a regimen for treating HLHS. In the case of HLHS, the injection system can be used, for example, to inject stem cells into the epicardium of the right ventricle. This treatment technique for HLHS may reduce the need for a heart transplant, or may postpone the need for a transplant. The systems and methods provided herein may also be used to treat other conditions such as congenital heart disease or valve dysfunction that results in heart failure and may benefit from local and focal stem cell therapy in which a minimal invasive delivery strategy is feasible.

Figure 1:
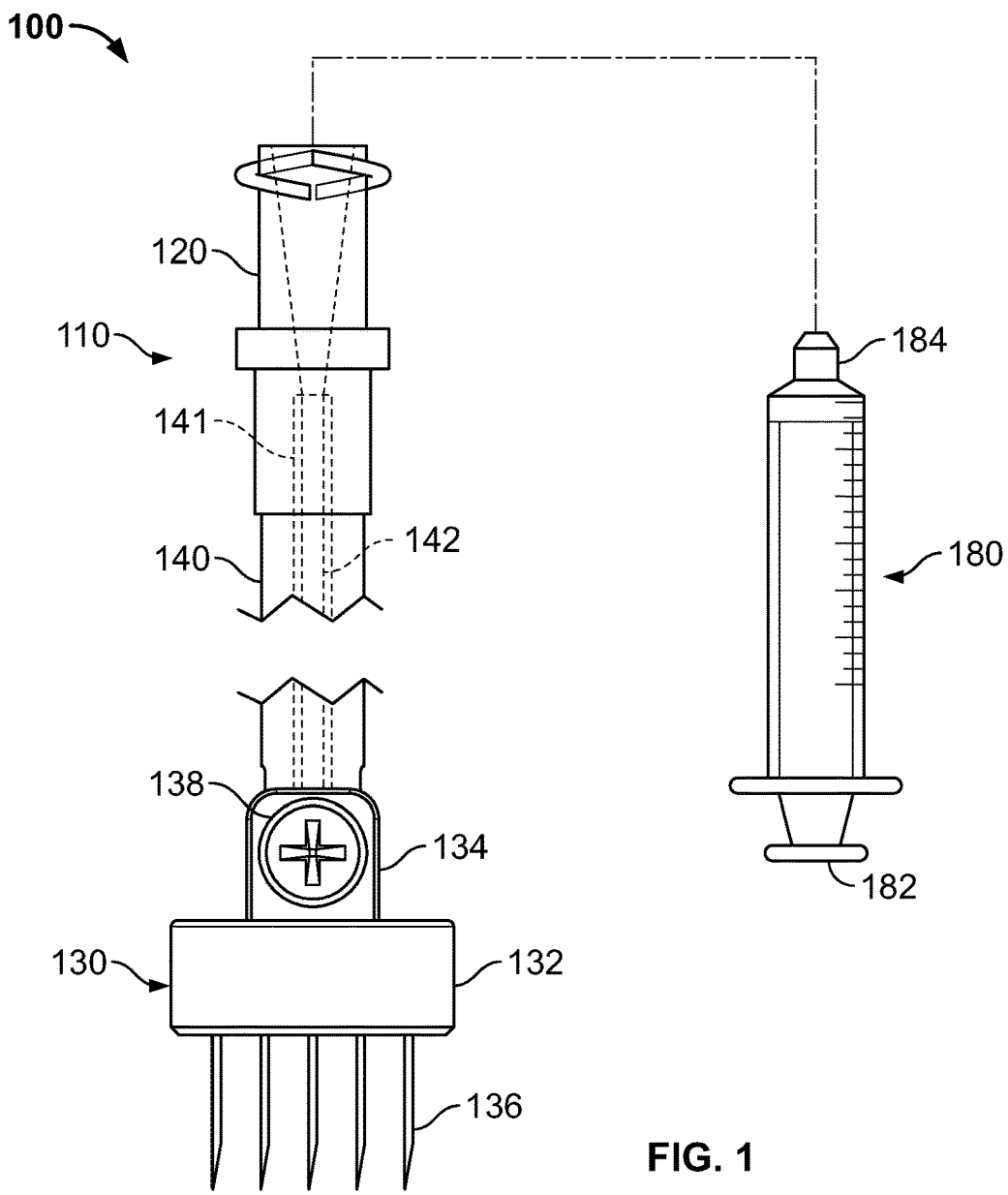
FIG. 1 is an exploded side view of a stem cell injection system, in accordance with some embodiments provided herein.

Referring to FIG. 1, an example stem cell injection system 100 can include an injection device 110 that is releasably coupleable with a syringe 180. Syringe 180 can contain fluidic material for injection. For instance, in an example implementation syringe 180 contains stem cell material for injection into the tissue of a patient as part of a regenerative medicine treatment regimen.

In the depicted embodiment, injection device 110 includes a proximal connector 120, a distal end portion 130, and a barrel 140. Barrel 140 interconnects proximal connector 120 and distal end portion 130. Barrel 140 is rigidly connected to proximal connector 120. In the depicted embodiment, barrel 140 is pivotably connected to distal end portion 130, but this feature is optional.

Injection device 110 can be constructed of various types of metallic or polymeric materials. For example, polymeric materials such as, but not limited, to polycarbonate, polyvinyl chloride (PVC), polyethylene, polypropylene, polymethyl methacrylate, polystyrene, acrylonitrile butadiene styrene (ABS), polyethylene, polypropylene, PEBEX, PICOFLEX, TECOFLEX, PTFE, ePTFE, FEP, PEEK, silicone, urethane, and the like can be used to construct injection device 110. Some portions of injection device 110 may be made of metallic materials including, but not limited to, stainless steels (e.g., austenitic 316 stainless steel or martensitic 440 and 420 stainless steels), titanium, titanium alloys (e.g., Ti6A14V), nitinol, aluminum, and the like, or combinations thereof. In some embodiments, at least some portions of injection device 100 are transparent.

In the depicted embodiment, proximal connector 120 is configured to couple with syringe 180. The coupling can be performed using a variety of types of connections. In some embodiments, a threaded connection is used between proximal connector 120 and syringe 180. For example, a luer fitting connection or bayoneted connection can be used. In some embodiments, a septum can be included in proximal connector 120 and syringe 180 can pierce the septum and dispense its contents therethrough. In some embodiments, a compression connection between proximal connector 120 and syringe 180 can be used. For example, at least the distal end portion of syringe 180 can be installed in an interior of proximal connector 120 so that the outer diameter of the distal tip 184 of syringe 180 is compressively contained within a resilient coupling member, such as an O-ring, within the interior of proximal connector 120. Other suitable techniques for coupling proximal connector 120 and syringe 180 can also be used.

The coupling between proximal connector 120 and syringe 180 establishes fluid communication between the interior of syringe 180 and a lumen of a tube 142 that is located within barrel 140. As such, the contents of syringe 180 can be dispensed from syringe 180 into tube 142.

Barrel 140 is rigidly attached (e.g., bonded, overmolded, threaded, etc.) to proximal connector 120 and pivotably attached to distal end portion 130. Barrel 140 includes a lumen 141 in which tube 142 is located. Tube 142 can be a metallic tube (e.g., stainless steel), or a flexible plastic tube (e.g., silicone), or combinations thereof, in some embodiments.

Figure 4:
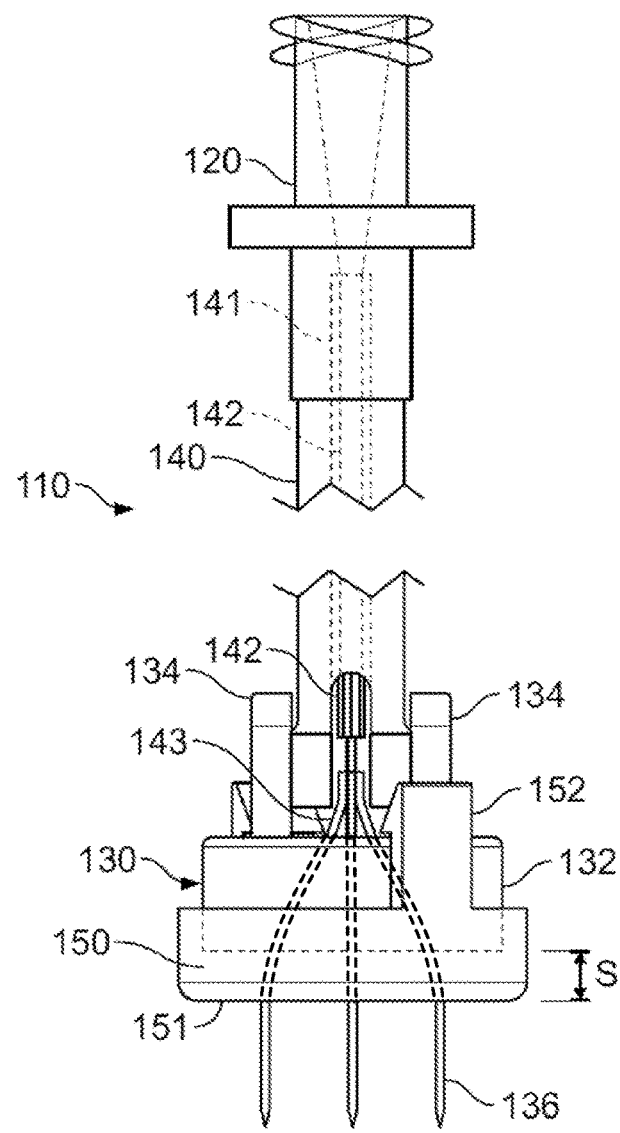
FIG. 4 is a side view of the stem cell injection device of FIG. 1 with a spacer installed on the distal end portion of the injection device.

Distal end portion 130 includes a body 132, clevis members 134, multiple needles 136, and clevis pins 138. In some embodiments, clevis members 134 are two proximal protrusions extending from body 132 (as best seen in FIG. 4). Clevis members 134 can be rigidly attached to body 132. In some embodiments, body 132 and clevis members 134 are formed as a monolithic component (e.g., a molded component in some embodiments). Needles 136 are rigidly attached to body 132, and extend distally therefrom. Needles 136 are hollow hypo tubes with beveled tips. In the depicted embodiment, a 29 gauge needle (0.3366 mm outer diameter) is used. In other embodiments, needles with other sizes (smaller or larger) can be used. In the depicted embodiment, needles 136 extend from body 132 by about 6 millimeters (mm) In other embodiments, needles 136 can extend from body 132 by greater or lesser distances.

Figure 2:
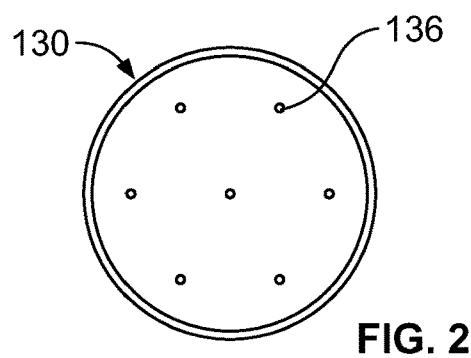
FIG. 2 is a distal end view showing the bottom of the stem cell injection system of FIG. 1.

Referring now to FIGS. 1 and 2, needles 136 can consist of multiple individual needles, such as the array of seven (7) individual needles 136 in the depicted embodiment. In other embodiments, other numbers of multiple individual needles can be used.

Individual needles 136 can be spaced from each other at equal distances. The equidistant spacing facilitates equal distribution of the injectate in the receiving tissue. In this embodiment, with seven (7) individual needles 136, needles 136 are arranged in a hexagonal pattern with a needle in the center of the hexagon. Any other patterns can be used, such as squares, triangles, rectangles, pentagons, heptagons, octagons, and so on.

To use stem cell injection system 100, needles 136 are inserted into a target tissue. Syringe 180 is then activated by pushing plunger 182. In response to the compression delivered by plunger 182, fluid from syringe 180 will flow into tube 142 and then into needles 136. A substantially equal volumetric amount of fluid will be emitted from each of the individual needles 136 and into the target tissue. Needles 136 can then be removed from the tissue. In some situations, stem cell injection system 100 can be repositioned to another area of target tissue, and the injection process can be repeated as many times as necessary to treat the totality of tissue as desired.

In some embodiments, stem cell injection system 100 is configured to have only a small amount of residual injectate material remaining in stem cell injection system 100 after the system has been used. Dead space, that volume within the stem cell injection system 100 that can contain residual injectate material, has been minimized by having the syringe go directly into the multiple needle lumens and by avoiding an unnecessary reservoir within the apparatus. This minimized space allows the effective use of potentially limited quantity of cell-based solutions used in the regenerative treatment, yet enables a hand-held device to be used in a minimally invasive procedure.

Distal end portion 130 also includes clevis pins 138. Clevis pins 138 facilitate a pivotable connection between clevis members 134 and barrel 140.

Figure 3:
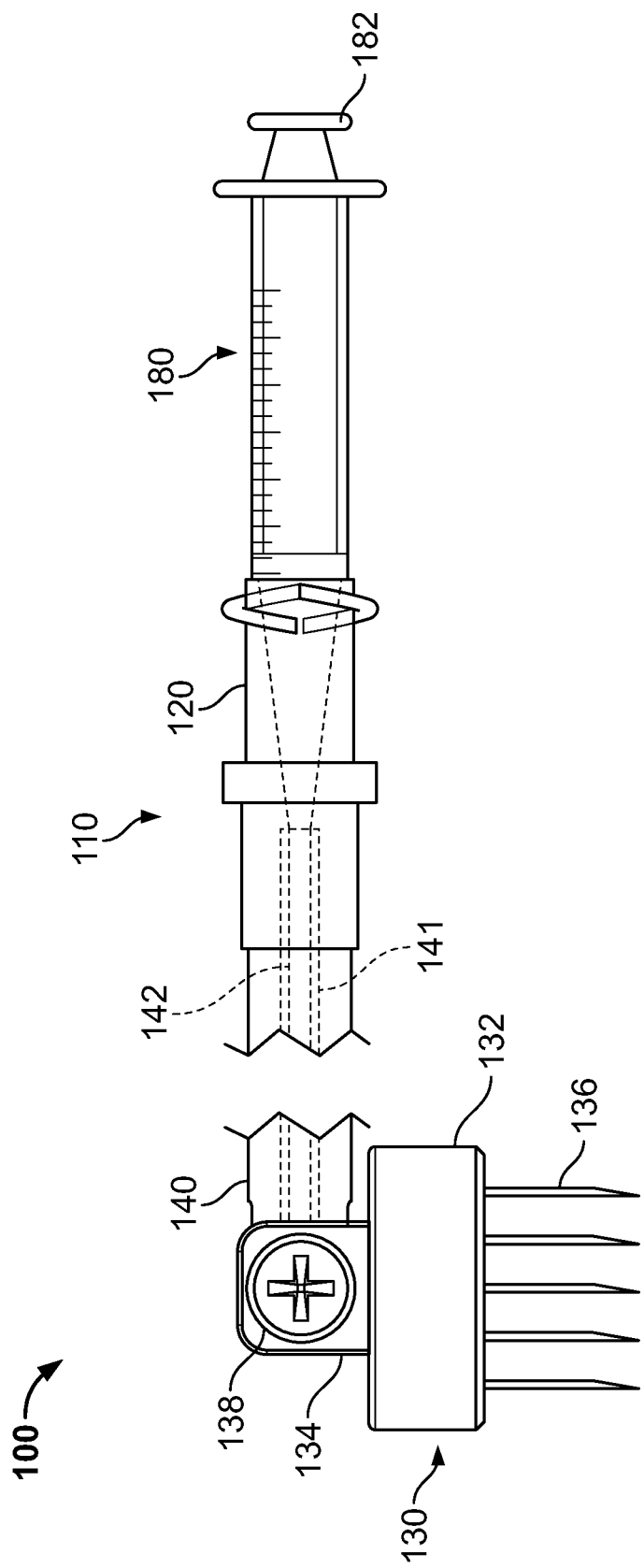
FIG. 3 is a side view of the stem cell injection system of FIG. 1 with the barrel of the injection device configured at a 90° angle in relation to the distal end portion of the injection device.

Referring now to FIG. 3, stem cell injection system 100 is shown in a right angle configuration. That is, barrel 140 has been pivoted in relation to distal end portion 130 by about 90° as compared to the linear configuration between barrel 140 and distal end portion 130 shown in FIG. 1. In some embodiments, barrel 140 can pivot in relation to distal end portion 130 through an arc of about 180°. The ability to pivot barrel 140 in relation to distal end portion 130 allows stem cell injection system 100 to be flexibly configured in various orientations to thereby suit a variety of different access paths, patients, and target tissue types.

In some embodiments, barrel 140 is detained at particular locations along its arcuate path relative to distal end portion 130. For example, in some embodiments, the connection between barrel 140 and distal end portion 130 includes a snap-lock detent mechanism such that barrel 140 is semi-rigidly detained in certain orientations relative to the distal end portion 130 (e.g., at about every 15° of arcuate pivot). In other embodiments, the detent can be at every 10°, 30°, 45°, 90°, or any other suitable relative angular orientation.

Figure 5:
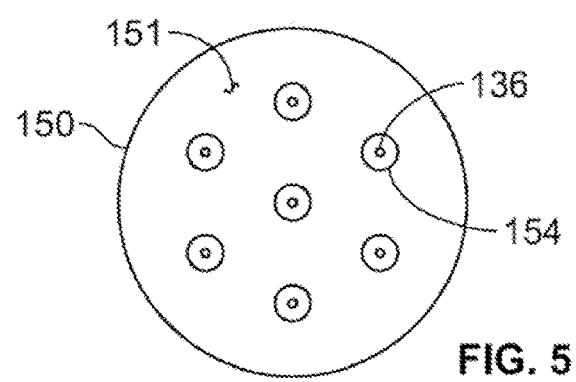
FIG. 5 is a distal end view showing the bottom of the stem cell injection system of FIG. 4.

Referring now to FIGS. 4 and 5, injection device 110 can optionally include a spacer 150. Spacer 150 can be releasably coupleable to distal end portion 130. For example, in the depicted embodiment spacer 150 includes two opposing flexible barbed tabs 152 that snap over body 132 of distal end portion 130. In other embodiments, other types of releasable coupling techniques can be used between spacer 130 and distal end portion 130, such as a threaded connection, a bayonet-type connection, a press-fit, and the like.

Spacer 150 includes multiple clearance holes 154. Clearance holes 154 are located in spacer 150 so as to allow needles 136 to protrude through spacer 150 in an unencumbered manner.

Spacer 150 reduces the exposed length of needles 136. More specifically, spacer 150 reduces the exposed length of needles 136 by a distance of "S" as shown in FIG. 4. The distance "S" can be whatever is desired by a clinician operator of injection device 110. In some cases an assortment of spacers 150 with different distances "S" can be available to the clinician operator of injection device 110 so that the spacer with the particular distance "S" can be selected as desired for a particular situation. In some embodiments, multiple spacers can be stacked together to create additional distances "S."

Using spacer 150, the maximum insertion depth of needles 136 can be limited/established as desired. In turn, the dispensation depth of the injectate can be selectively controlled. For example, when injection device 110 is inserted into a target tissue area, injection device 110 can be inserted until the face 151 of spacer 150 makes contact with the tissue. Therefore, substantially the entire exposed length of needles 136 (a known distance) can be inserted into the tissue. When a deeper dispensation depth is desired, a spacer 150 with a less distance "S" can be selected. Conversely, when a shallower dispensation depth is desired, a spacer 150 with a greater distance "S" can be selected.

FIG. 4 also illustrates the dividing of tube 142 into multiple sub-tubes 143. Multiple sub-tubes 143 interconnect tube 142 to needles 136. That is, each individual sub-tube of the multiple sub-tubes 143 is in fluid communication with one individual needle of the needles 136. In alternative embodiments, a manifold is contained within body 132. In some such embodiments, tube 142 is confluent with the manifold and the manifold is configured to divide a substantially equal flow amount of injectate to each individual needle of needles 136.

In some embodiments, devices other than syringe 180 are used as the source of the injectate. For example, in some embodiments a syringe-type device can be built into the barrel 140, rather than being separable as described above. In other embodiments, a pump device can be connected to injection device 110.

In some alternative embodiments, the designs of the stem cell injection systems provided herein can be miniaturized and used with a scope rather than hand-held device. Such miniaturized embodiments can facilitate the diffusion of cell-based products into tissue such as the heart in a local and focal approach. This modification would enable the concept of the diffusion needle pattern and minimal deadspace to be retrofitted on other minimally invasive devices that are designed to gain access to diseased tissues with minimal surgical approach avoiding vascular access.

Figure 6:
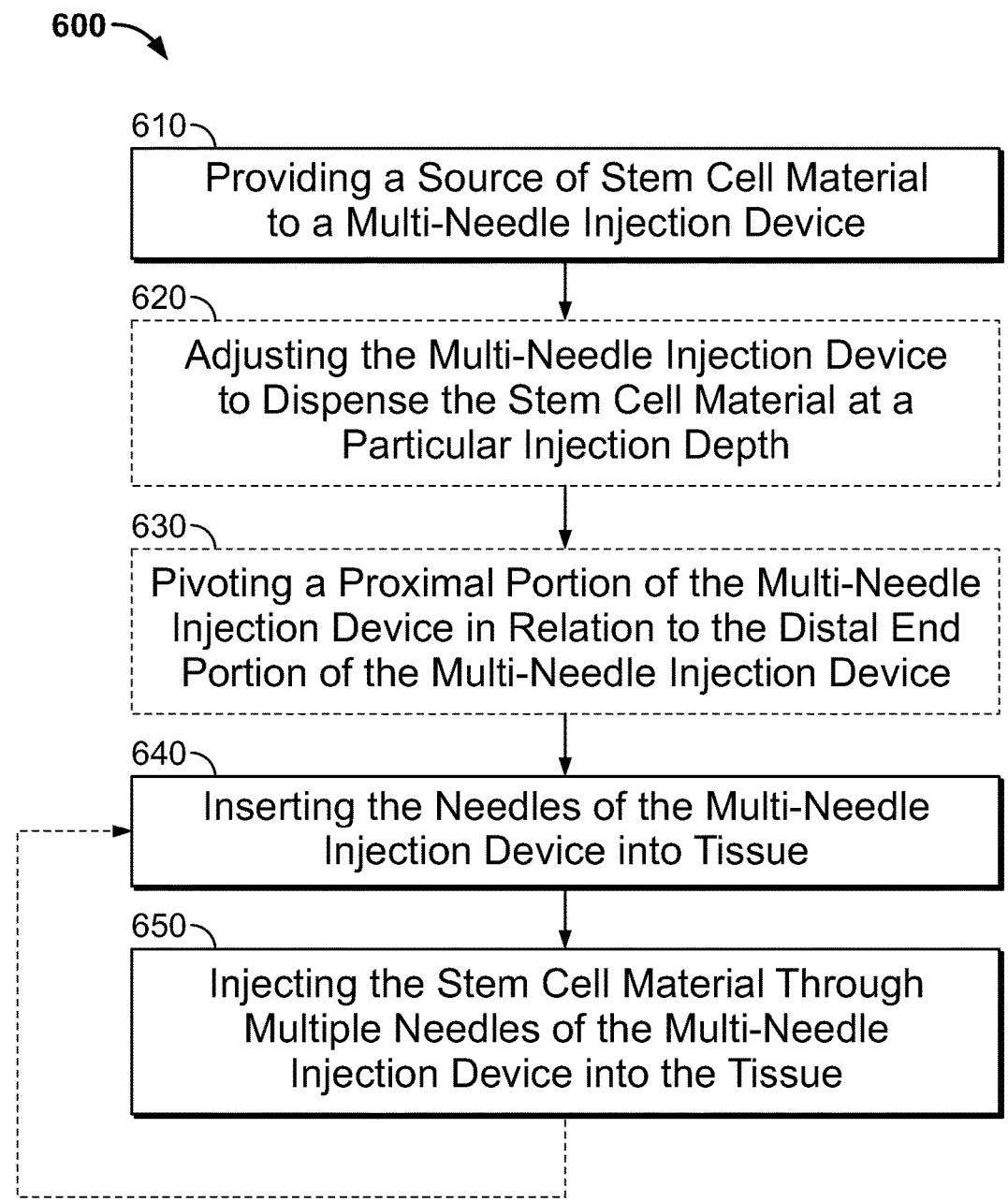
FIG. 6 is a flowchart of a method for injecting stem cell material into tissue, in accordance with some embodiments provided herein.

Referring to FIG. 6, a flowchart of a method 600 for treating a tissue with stem cell material is provided.

At operation 610, a source of stem cell material is provided to a multi-needle injection device. This step is illustrated, for example, by the connection of syringe 180 to the injection device 110 as described above.

At operation 620, the multi-needle injection device is optionally adjusted so as to selectively control the injection depth of the stem cell material. This step can be performed, for example, by installing spacer 150 on distal end portion 130 as described above.

At operation 630, the proximal portion of the multi-needle injection device is optionally pivoted in relation to the distal end portion of the multi-needle injection device. For example, this step is illustrated above in regard to FIG. 2 as compared to FIG. 1. It should be understood that pivot angles other than 90° can be selected.

At operation 640, the needles of the multi-needle injection device are inserted into a target tissue area. For example, in some implementations the target tissue area is the epicardium of the right ventricle. Other tissue areas can be similarly treated.

At operation 650 the stem cell material is dispensed from the source of stem cell material, through the multiple needles of the multi-needle injection device, and into the target tissue area. The dispensation is substantially uniform in terms of the amount dispensed from each individual needle and the area distribution (because the needles are uniformly spaced apart from each other), as described above.

In some circumstances, the steps of inserting 640 and injecting 650 are repeated in another tissue area, as desired by a clinician operator, so as to treat the totality of the target tissue area.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A device for injecting stem cell material into a tissue, the device comprising:
   a proximal end coupling portion that is configured to releasably couple with a syringe containing the stem cell material;
   a barrel that is rigidly coupled to the coupling portion, the barrel including a flexible tube therein, the flexible tube being configured to receive and convey the stem cell material when the syringe is activated to dispense the stem cell material therefrom;
   a distal end portion that is pivotably coupled to the barrel, wherein pivoting the distal end portion in relation to the barrel causes bending of the flexible tube, the distal end portion including multiple needles extending distally from a body of the distal end portion, wherein the multiple needles are configured for insertion into the tissue; and
   multiple sub-tubes fluidically interconnecting the flexible tube and the multiple needles,
   wherein the flexible tube is fluidically connected to each sub-tube of the multiple sub-tubes, and wherein each sub-tube of the multiple sub-tubes is fluidically connected to a respective individual needle of the multiple needles such that a substantially equal amount of stem cell material will be dispensed from each individual needle when the syringe is activated to dispense the stem cell material therefrom.

2. The device of claim 1, wherein the barrel is pivotable in relation to the distal end portion through an arc of about 180 degrees.

3. The device of claim 1, wherein the multiple needles includes four or more individual needles.

4. The device of claim 1, wherein the multiple needles includes seven or more individual needles.

5. A system for injecting stem cell material into a tissue, the system comprising:

a syringe that is configured to contain and dispense the stem cell material therefrom; and an injection device comprising:

a proximal end coupling portion that is configured to releasably couple with the syringe;

a barrel that is rigidly coupled to the coupling portion, the barrel including a flexible tube therein, the flexible tube being configured to receive and convey the stem cell material when the syringe is activated to dispense the stem cell material therefrom;

a distal end portion that is pivotably coupled to the barrel, wherein pivoting the distal end portion in relation to the barrel causes bending of the flexible tube, the distal end portion including multiple needles extending distally from a body of the distal end portion, wherein the multiple needles are configured for insertion into the tissue; and multiple sub-tubes fluidically interconnecting the flexible tube and the multiple needles, wherein the flexible tube is fluidically connected to each sub-tube of the multiple sub-tubes, and wherein each sub-tube of the multiple sub-tubes is fluidically connected to a respective individual needle of the multiple needles such that a substantially equal amount of stem cell material will be dispensed from each individual needle when the syringe is activated to dispense the stem cell material therefrom.

6. The system of claim 5, further comprising a spacer, the spacer being coupleable to the distal end portion, the spacer being configured to establish a maximum injection depth of the stem cell material into the tissue.

7. The system of claim 6, wherein the barrel is pivotable in relation to the distal end portion through an arc of about 180 degrees.

8. The system of claim 6, wherein the multiple needles includes four or more individual needles.

9. The system of claim 6, wherein the multiple needles includes seven or more individual needles.

\* \* \* \* \*